(12) United States Patent
Mao et al.

(10) Patent No.: US 11,414,795 B2
(45) Date of Patent: Aug. 16, 2022

(54) STABLE CONDUCTIVE MYOCARDIAL PATCH WITH NEGATIVE POISSON'S RATIO STRUCTURE AND PREPARATION METHOD THEREOF

(71) Applicant: DONGHUA UNIVERSITY, Shanghai (CN)

(72) Inventors: Jifu Mao, Shanghai (CN); Yimeng Li, Shanghai (CN); Yaya Gao, Shanghai (CN); Chaojing Li, Shanghai (CN); Fujun Wang, Shanghai (CN); Lu Wang, Shanghai (CN)

(73) Assignee: DONGHUA UNIVERSITY, Shanghai (CN)

( * ) Notice: Subject to any disclaimer, the term of this patent is extended or adjusted under 35 U.S.C. 154(b) by 0 days.

(21) Appl. No.: 17/324,127

(22) Filed: May 19, 2021

(65) Prior Publication Data

US 2021/0404097 A1 Dec. 30, 2021

(30) Foreign Application Priority Data

Jun. 24, 2020 (CN) .......................... 202010590534.X

(51) Int. Cl.
*D03D 13/00* (2006.01)
*D03D 15/283* (2021.01)
(Continued)

(52) U.S. Cl.
CPC ......... *D03D 13/004* (2013.01); *A61F 2/2481* (2013.01); *C08F 2/04* (2013.01);
(Continued)

(58) Field of Classification Search
CPC .. A61F 2/2481; D03D 13/004; D03D 15/283; D03D 15/56; D03D 17/00; D04B 1/10; D04B 1/18
See application file for complete search history.

(56) References Cited

U.S. PATENT DOCUMENTS

| | | | | | |
|---|---|---|---|---|---|
| 5,853,794 | A | * | 12/1998 | Melody | H01G 9/025 |
| | | | | | 427/58 |
| 2011/0046715 | A1 | * | 2/2011 | Ugbolue | D04B 21/12 |
| | | | | | 623/1.15 |

FOREIGN PATENT DOCUMENTS

| CN | 106149150 A | * | 11/2016 | ........... D03D 13/004 |
|---|---|---|---|---|
| CN | 108570758 A | | 9/2018 | |

OTHER PUBLICATIONS

Kapnisi, Michaella, et al. "Auxetic Cardiac Patches with Tunable Mechanical and Conductive Properties toward Treating Myocardial Infarction." Advanced Functional Materials, vol. 28, No. 21, Apr. 10, 2018, https://doi.org/10.1002/adfm.201800618. (Year: 2018).*

(Continued)

*Primary Examiner* — Larissa Rowe Emrich
(74) *Attorney, Agent, or Firm* — Bayramoglu Law Offices LLC

(57) ABSTRACT

A stable conductive myocardial patch with a negative Poisson's ratio structure is provided. The preparation method includes preparing a myocardial patch substrate with concave polygons as the structural units by weaving or knitting, and then a conductive coating is coated on the surface of the substrate. Alternatively, the yarns can be processed into conductive coated yarns first, and then used as the raw material to weave or knit a stable conductive myocardial patch with a negative Poisson's ratio structure. The prepared myocardial patch has a relative resistance change of less than 5% at 50% tensile strain. When the strain of the structural units is within 50%, the fabric exhibits a negative Poisson's ratio structure, which expands in the perpendicular direction of the tensile load. The fabric exhibits a negative Poisson's ratio effect and anisotropy of Young's modulus, which matches the mechanical behavior of natural myocardium.

14 Claims, 3 Drawing Sheets

(51) Int. Cl.
| | |
|---|---|
| *D03D 15/56* | (2021.01) |
| *A61F 2/24* | (2006.01) |
| *C09D 5/24* | (2006.01) |
| *C09D 139/04* | (2006.01) |
| *D03D 17/00* | (2006.01) |
| *C08F 2/04* | (2006.01) |
| *C08F 126/06* | (2006.01) |
| *D04B 1/10* | (2006.01) |
| *D04B 1/18* | (2006.01) |
| *D02G 3/02* | (2006.01) |
| *D02G 3/32* | (2006.01) |
| *D02G 3/44* | (2006.01) |

(52) U.S. Cl.
CPC .............. *C08F 126/06* (2013.01); *C09D 5/24* (2013.01); *C09D 139/04* (2013.01); *D03D 15/283* (2021.01); *D03D 15/56* (2021.01); *D03D 17/00* (2013.01); *D04B 1/10* (2013.01); *D04B 1/18* (2013.01); *D10B 2331/041* (2013.01); *D10B 2331/10* (2013.01); *D10B 2401/061* (2013.01); *D10B 2403/03* (2013.01); *D10B 2509/06* (2013.01)

(56) References Cited

OTHER PUBLICATIONS

"CN106149150_Machine Translation" is a machine translation of CN-106149150-A. (Year: 2016).*
Zulifqar, Adeel, and Hong Hu. "Development of Bi-Stretch Auxetic Woven Fabrics Based on Re-Entrant Hexagonal Geometry." Physica Status Solidi (b), vol. 256, No. 1, 2018, p. 1800172., https://doi.org/10.1002/pssb.201800172. (Year: 2018).*
Jiyang Chen, et al., A Biodegradable Knitted Cardiac Patch For Myocardium Regeneration Using Cardiosphere-Derived Cells (CDCs), Journal of Donghua University, 2017, pp. 310-315, vol. 34 No. 2.
Michaella Kapnisi, et al., Auxetic Cardiac Patches with Tunable Mechanical and Conductive Properties toward Treating Myocardial Infarction, Advanced Functional Materials, 2018, pp. 1-12, 28.

* cited by examiner

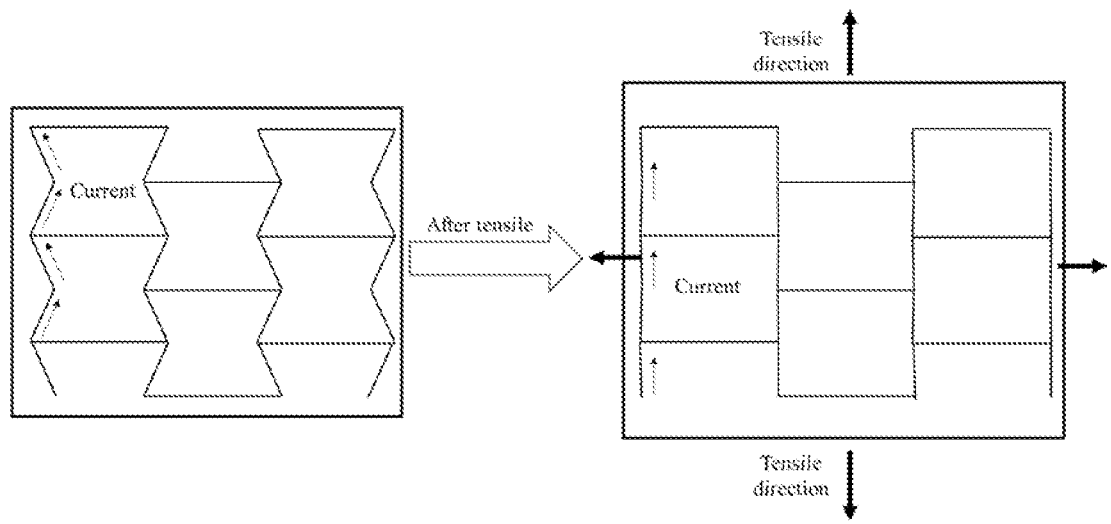
FIG. 1
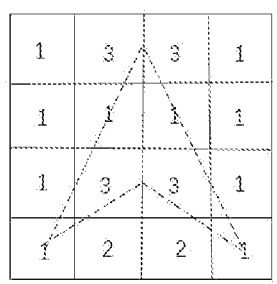 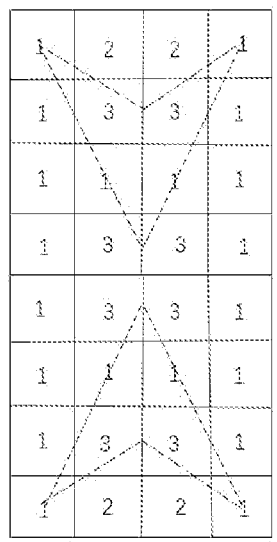 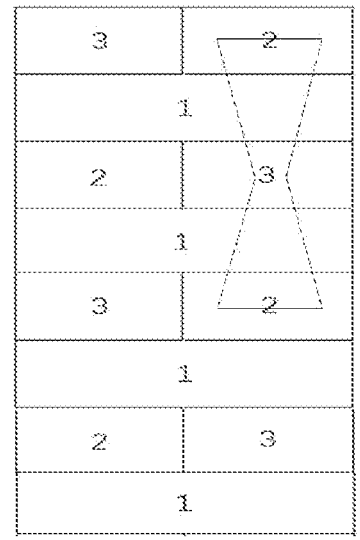
FIG. 2A  FIG. 2B  FIG. 2C

STABLE CONDUCTIVE MYOCARDIAL PATCH WITH NEGATIVE POISSON'S RATIO STRUCTURE AND PREPARATION METHOD THEREOF

CROSS REFERENCE TO THE RELATED APPLICATIONS

This application is based upon and claims priority to Chinese Patent Application No. 202010590534.X, filed on Jun. 24, 2020, the entire contents of which are incorporated herein by reference.

TECHNICAL FIELD

The invention belongs to the technical field of biomedical materials and relates to a stable conductive myocardial patch with a negative Poisson's ratio structure and a preparation method thereof.

BACKGROUND

Cardiovascular disease is one of the major diseases leading to human deaths in the world, accounting for more than 40% of deaths from diseases. Among them, myocardial infarction and other types of ischemic heart disease are the leading causes of death. Death toll from myocardial infarction and its complications in China has exceeded 1 million every year, and the incidence rate is increasing year by year. Although the existing interventional therapy and thrombolytic reinfusion therapy have significantly reduced the mortality of acute myocardial infarction. However, the damaged myocardium is necrotic and cannot be regenerated, and it will be replaced by the surrounding connective tissue to form scar tissue, which cannot be repaired by surgery. The mortality rate of complications in the decompensated period of myocardial infarction is still high. The tissue-engineered myocardial patch is a composite of cardiomyogenic seed cells and scaffold biomaterials, which can be used for transplantation, repair, or replacement of autologous myocardium. A tissue-engineered myocardial patch provides a promising technique for repairing damaged myocardium.

Electrical conductivity is an important factor in maintaining heart function. Scar tissue after myocardial infarction interferes with the propagation of electrical signals. Studies have proved that the introduction of conductive polymers into the myocardial patch can help electrical signal conduction and vascular regeneration in the area of myocardial infarction. However, existing studies have neglected that the strain of the conductive myocardial patch caused by the contraction and relaxation of the native heart will cause substantial changes of electrical resistance. Studies have shown that the electrical conductivity of the conductive myocardial patch has an important impact on the amplitude and frequency of the electrical signal transmission of myocardial cells and the frequency of $Ca^{2+}$ transients. Changes in the electrical conductivity of the myocardial patch may cause differences in the contraction frequency of myocardium. Therefore, the stability of electrical conduction plays a vital role in maintaining the synchronized contractility of myocardium.

The mechanical properties of the myocardial patch are also critical to heart function. It is generally believed that the mechanical properties of the myocardial patch should match the healthy myocardium. The Young's modulus of the natural heart varies from 0.02 to 0.5 MPa and has obvious mechanical anisotropy. In addition, Poisson's ratio is an important mechanical property that is often overlooked. Most materials have a positive Poisson's ratio, shown as shrinking in the transverse direction when being stretched longitudinally. Materials with negative Poisson's ratio can expand in multiple directions at the same time, thereby affecting the synclastic curvature and shear strength. Studies have pointed out that biomaterials with negative or zero Poisson's ratio may be most suitable for simulating the behavior of natural tissues.

At present, the existing conductive myocardial patches are mainly designed to restore electrical signal conduction across the infarcted myocardium. The similitude of the electrical conductivity between the myocardial patch and myocardium in a static state has been extensively studied, but it has been neglected that the electrical resistance of the conductive myocardial patch will change due to heart pumping, which will affect the transmission of electrical signals. There are mainly two ways to grant the myocardial patch conductive performance. The most commonly used method is to deposit a conductive layer on the surface of the myocardial patch substrate. In order to ensure good biocompatibility, conductive materials are mostly conductive polymers. However, due to the inherent defect in mechanical performance of conductive polymers, it is difficult to match with the tensile properties of the myocardial patch substrate. This difference causes the conductive layer to crack when the conductive myocardial patch is stretched, which leads to changes in the electrical resistance of the conductive myocardial patch and affects the transmission of electrical signals. In more serious cases, the conductive coating may be completely broken, which will cause the conductive myocardial patch to completely lose the electrical signal transmission ability when the myocardium is beating. Another way to prepare a conductive myocardial patch is to use hybrid of conductive materials and biomaterials through a spinning or gel process. In this way, the conductive material is evenly dispersed inside the myocardial patch, and the penetration of the conductive material in the fiber or gel gives the patch electroconductivity. The conductive performance is still maintained under large deformation, and insulativity caused by the mismatch of the mechanical performance between the conductive material and the supporting material is basically avoided. However, when the substrate is stretched, the conductive material will concomitantly elongate along the stretch direction and shrink in the structural unit direction. During such period, the total path length of electrons through the patch is significantly increased, and the cross-sectional area is significantly reduced, which leads to a decrease in the conductivity of the patch and hinders the transmission of electrical signals. In addition, in order to ensure the biocompatibility of the myocardial patch, the existing myocardial patch mostly uses materials such as collagen and alginate, whose mechanical properties are difficult to meet the requirements of the traction force caused by heartbeat. Even if the myocardial patch prepared by electrospinning technology has a rather good mechanical property, a matching mechanical anisotropy and Poisson's ratio performance of the myocardial patch with the natural myocardium is still ignored.

Therefore, it is of great significance to develop a preparation method and product of a myocardial patch with conductivity stability and matching electrical and mechanical properties of natural myocardium.

SUMMARY

This invention provides a stably conductive myocardial patch with a negative Poisson's ratio structure and a preparation method thereof and aims to solve the problem that the conductive myocardial patch in the prior art is difficult to maintain stable conductive performance after implantation and to match the electrical and mechanical behavior of the natural myocardium.

In order to solve the above-mentioned problems, the scheme adopted by this invention is as follows:

A stably conductive myocardial patch with negative Poisson's ratio structure, a knitted fabric or woven fabric with a concave polygon as a structural unit; the knitted fabric or woven fabric is composed of yarns and conductive coatings on the surface; the unbalanced structure of the structural unit will shrink and fold to form a concave polygonal structure after being removed from the machine. The knitted fabric or woven fabric can be woven on a large scale, and it can be tailored into the customized size of the patient's myocardial infarction area in practical application; it can also be woven according to the size of the patient's myocardial infarction area.

The initial conductivity of the myocardial patch is 1-10 S/m, and it exhibits stable conductivity during heart contraction, that is, the relative resistance change $(R-R_0)/R$ (where $R_0$ is the initial resistance, and R is the resistance after being stretched) is less than 5% at 50% tensile strain. The deformation rate of natural myocardium is about 10-20%. When the strain of the structural units is within 50%, the fabric presents a negative Poisson's ratio performance. As the stretch rate increases, the Poisson's ratio of the fabric gradually increases from a minimum Poisson's ratio of –0.5 (The minimum Poisson's ratio of knitted fabric is –0.5, and that of woven fabric is –0.1), and the structural units expand in the perpendicular direction of the tensile load. The anisotropy ratio of the mechanical properties of natural myocardium is 1.9-3.9. The myocardial patch showed anisotropy of Young's modulus, and the anisotropy ratio is 1.99-5.71. Young's modulus of the myocardial patch is 0.4-8 MPa, which matches the mechanical behavior of natural myocardium. The myocardial patch has a stable conductive coating, which can effectively restore the electrical signal path of the damaged myocardium and stably transmit electrical signals in the dynamic environment of heart beating. As the conductive coating is stretched, the concave folded structure is unfolded, and a spatial reconstruction occurs. The path and cross-sectional area of electrons in the conductive myocardial patch do not change significantly. Therefore, the conductive myocardial patch exhibits strain insensitivity.

As the preferred method:

A stable conductive myocardial patch with a negative Poisson's ratio structure, wherein the structural unit is composed of yarns with different elasticities, and the weaves formed by the elastic yarns pull their surrounding weaves to shrink and fold.

A stable conductive myocardial patch with a negative Poisson's ratio structure, wherein the concave polygonal structural units in the woven fabric are composed of weaves 1, 2, and 3 interwoven by yarns with different elasticities; among them, weave 1, 2, and 3 have sequentially decreasing fabric densities.

The structural units in the knitted fabric are half loops and half floats in the course where the elastic yarns are located; the elastic yarns that form the float have a higher shrinkage rate than the loop-forming yarns.

A stable conductive myocardial patch with a negative Poisson's ratio structure, wherein weave 1 is a plain weave, weave 2 is a twill weave (Preferably ¼ twill weave) or a satin weave (Preferably 5/3 satin weave) which is relatively loose compared with plain weave, and the weave 3 is a weave in which the warp yarns alternately float on the weft yarns, which is the loosest among the three fabric structures.

The densities of warp and weft are preferably 30 and 25 yarns/cm.

After the fabric is relaxed from the machine, weave 3 will exhibit the largest contraction, pulling its surrounding weave, and weave 1 is the most tightly interwoven structure, which can prevent the fabric from excessive shrinking, thereby achieving a concave polygonal structure.

A stable conductive myocardial patch with a negative Poisson's ratio structure, wherein the warp yarns of the woven fabric are alternatingly arranged by elastic yarns and inelastic yarns with a number ratio of 1:1, and the weft yarns are composed of elastic yarns separately or alternatingly arranged by elastic yarns and inelastic yarns with a number ratio of 1:1; the yarns in the knitted fabric are composed of inelastic ones and elastic ones with a number ratio of 2:1.

The concave structure of the structural unit in the knitted fabric is realized by the different shrinkage of elastic yarns on one course and the different stitch densities on different wales. Taking the concave hexagon as an example, the elastic yarns floating in the course are highly contractible, so the elastic yarns forming loops will shrink and fold toward the floating line to form a concave structure. The non-elastic yarns adjacent to the elastic yarns have tightly plain stitches to prevent the fabric from excessive shrinking.

A stable conductive myocardial patch with a negative Poisson's ratio structure, wherein the chemical composition of the elastic yarn is polycaprolactone or polyurethane, and the non-elastic yarn is polylactic acid.

A stable conductive myocardial patch with a negative Poisson's ratio structure, wherein the concave polygon is a concave quadrilateral, a symmetrical concave quadrilateral, or a concave hexagon.

When the structural unit is a concave quadrilateral or a symmetrical concave quadrilateral, weave 3 will shrink and deform greatly after being relaxed from the machine, resulting in shrinkage along the radial direction of the fabric, forming a concave quadrilateral structure. When the structural unit is a concave hexagon, weave 3 shrinks and deforms the most, pulling the surrounding weaves, and the tight structure of the weave 1 can prevent the fabric from shrinking in the radial direction. Thus, a concave hexagonal structure that shrinks along the weft direction of the fabric is obtained.

A stable conductive myocardial patch with a negative Poisson's ratio structure, wherein the conductive coating is mainly made by the polymerization reaction of conductive polymer monomers, dopants, and oxidants.

A stable conductive myocardial patch with a negative Poisson's ratio structure, wherein when the conductive material monomer is pyrrole, the dopant is sodium dodecylbenzene sulfonate or cetyltrimethylammonium bromide, and the oxidant is ammonium persulfate or ferric chloride;

or, when the conductive material monomer is aniline, the dopant is hydrochloric acid, sulfuric acid, nitric acid, camphorsulfonic acid or sodium dodecylbenzene sulfonate, and the oxidant is ammonium persulfate, potassium dichromate, ferric chloride, or potassium iodate;

or, when the conductive material monomer is thiophene, the dopant is sodium dodecylbenzene sulfonate or cetyltrimethylammonium bromide, and the oxidant is iron trichloride, copper perchlorate, aluminum trichloride, or ammonium sulfate.

The method for preparing a stable conductive myocardial patch with a negative Poisson's ratio structure, characterized in that: the myocardial patch substrate with concave polygonal structural units is manufactured by weaving or knitting, and then a conductive coating is coated on the surface of the substrate by coating and in-situ polymerization to obtain a conductive and stable myocardial patch with a negative Poisson's ratio structure;

or, the yarns can be processed into conductive coated yarns first by coating and in-situ polymerization, and then the conductive yarns are used as the raw material to weave or knit a stable conductive myocardial patch with a negative Poisson's ratio structure.

The process of the in-situ polymerization method is: oxidants and dopants are coated on fabrics or yarns, and then conductive polymer monomers are introduced in form of liquid or gas phase for polymerization; or, the conductive polymer monomer and dopant are coated on the fabric or yarns, and then the oxidant is coated for initiating polymerization.

Alternatively, the conductive polymer monomer is added to the oxidant and dopant to polymerize and then dried to prepare the conductive material powder; finally, the conductive material powder is coated on the fabric or yarns.

As the preferred method:

The method for preparing a stable conductive myocardial patch with a negative Poisson's ratio structure, wherein the process of fabricating the conductive polymer layer onto the myocardial patch substrate by the in-situ polymerization method is:

(1) The oxidant and dopant (the mass ratio is 1:1-5:1) are added to the 10-40 wt % (preferably 30 wt %) polyurethane solution and stirred evenly;

(2) The surface of the myocardial patch substrate is coated with polyurethane solution 1-10 times (preferably 5 times);

(3) The coated substrate is fumigated with conductive polymer monomer at 0-60° C. (preferably 4° C.) for 1-24 h (preferably 12 h).

The process of fabricating the conductive polymer layer onto the yarns by the in-situ polymerization method is:

(1) The conductive polymer monomer and dopant (the mass ratio is 1:3-1:1) are added to the 10-40 wt % (preferably 30 wt %) polyurethane solution and stirred evenly;

(2) The yarns are immersed in the mixed solution for 1-30 min (preferably 5 min);

(3) The coated yarns are immersed in or coated with the oxidant solution (the concentration is 0.1-1 M) at 0-60° C. (preferably 4° C.) for 1-24 h (preferably 12 h).

(4) After washing with deionized water for 1 to 5 times (preferably 3 times), the coated yarn is dried to obtain conductive yarns;

The process of surface coating is:

(1) The conductive polymer monomer and dopant (the mass ratio is 1:4-1:1) are added to the oxidant solution (the concentration is 0.1-1 M) and stirred, and then allowed to polymerize for 3-6 h (preferably 4 h);

(2) After polymerization, the conductive polymer powder is obtained by filtration and drying;

(3) A certain mass of conductive polymer powder (preferably 20 wt %) is added to the 10-40 wt % (preferably 30 wt %) polyurethane solution and stirred evenly;

(4) The surface of the myocardial patch substrates or yarns are coated with the mixed solution 1 to 10 times (preferably 5 times), and a stable conductive myocardial patch or conductive yarns with a negative Poisson's ratio structure is prepared after drying.

The method for preparing a stable conductive myocardial patch with a negative Poisson's ratio structure, characterized in that when weaving technology is used, the specific steps are as follows:

(1) The yarns or conductive yarns are woven on a loom (Preferably, rapier loom, air jet loom, etc.) with two kinds of weft yarn supplies and shedding mechanism (the shedding mechanism is a dobby shedding mechanism, a jacquard shedding mechanism, etc. Preferably, the number of heald frames required for the concave quadrilateral structure is 13, and the number of heald frames required for the concave hexagon structure is 16 to obtain a fabric;

Different shrinkage effects can be produced in the weft direction by using weave structures with different shrinkage characteristics. Elastic yarns introduce elasticity into the fabric structure and act as return springs. Non-elastic yarns are used as stabilizing component, combining loose and tight weaves can introduce stretchability into the fabric structure and help maintain the transverse dimension of the fabric when being stretched;

(2) The fabric is soaked in deionized water at a temperature of 50-70° C. (preferably 60° C.) for 20-60 min (preferably 45 min), and dried in a drum at 60-100° C. (preferably 70° C.) for 30-60 min (preferably 60 min);

(3) The fabric is relaxed for 12-24 h to obtain a woven fabric.

When weaving, the warp yarns of different weaves pass through different heald frames in turn, and the movement of the heald frames drives the warp and weft yarns to move and interweave with the weft yarns. The repeated weaving pattern in the warp direction of the fabric is: the warp passes through the heald frame with an order in the alternating sequence of elastic yarn and non-elastic yarn, and when one structural unit is finished, the above-mentioned drawing-in processed is repeated. The repeated weaving pattern in the weft direction is: the warp yarns are separated up and down under the action of the heald frame to form a cloth-fell, then weft insertion is carried out, and finally the heald frame moves to form a weave structure. After weaving a structural unit, repeat the above steps to weave the next unit.

When using knitting technology, the specific steps are as follow:

(1) The yarns or conductive yarns are fed in and knitted on the computerized flat knitting machine to obtain the fabric;

(2) The fabric is soaked in deionized water at a temperature of 50-70° C. (preferably 60° C.) for 20-60 min (preferably 45 min), and dried in a drum at 60-100° C. (preferably 70° C.) for 30-60 min (preferably 60 min);

(3) The fabric is relaxed for 12-24 h to obtain a knitted fabric.

The specific application steps of using the above-mentioned stable conductive myocardial patch with negative Poisson's ratio structure for myocardial repair are as follows:

(1) The cardiomyocytes derived from human induced pluripotent stem cells are seeded on a conductive and stable myocardial patch with a negative Poisson's ratio structure. Cardiomyocytes are cultured in high-glucose Dulbecco's modified Eagle medium supplemented with 15% fetal bovine serum, 100 U/ml penicillin, and 100 ug/ml streptomycin. Cells are incubated at 37° C. under 5% $CO_2$, and the medium is changed every two days.

(2) A conductive myocardial patch with a negative Poisson's ratio structure loaded with cardiomyocytes is implanted into the patient's myocardial infarction area through surgery. After implanting biomaterials, the muscle and skin are stitched with sutures.

Preferably, the surgical method of implanting the conductive myocardial patch is thoracotomy or thoracoscopic assisted surgery.

The principle of this invention is as follows:

The myocardial patch is woven or knitted to produce a fabric with an unbalanced structure, and the fabric will naturally shrink and fold after being relaxed from the machine to form a concave polygonal structure to realize the negative Poisson's ratio effect of the fabric. In addition, the negative Poisson's ratio structural fabric has mechanical anisotropy, that is, Young's modulus in different directions is different. Before getting off the machine, apply a conductive coating to the fabric or use conductive fibers for weaving. After the fabric gets off the machine, the conductive layer will shrink and deform accordingly, forming a concave polygonal structure effect. When the conductive myocardial patch is deformed, the conductive coating can unfold with the concave structure of the myocardial patch and reconstruct spatially, but it will not produce obvious tensile deformation. When transmitting electrical signals, the cross-section and total path of the electrical signals flowing through the conductive coating do not change significantly, showing conductivity stability. The electrical conductivity of the myocardial patch does not change significantly with the heartbeat, and its electrical and mechanical properties match the natural myocardium, which can effectively promote the regeneration and functional recovery of the myocardium.

BENEFICIAL EFFECTS (1) The myocardial patch with negative Poisson's ratio structure in this invention has stable conductive performance when it is affected by strain caused by heartbeat. In the process of effectively restoring the electrical signal pathway of the damaged myocardium, it avoids the changes in the electrical conductivity of the conductive myocardial patch caused by the heartbeat;

(2) The stable conductive myocardial patch has excellent mechanical properties, a negative Poisson's ratio structure, and mechanical anisotropy, which matches the mechanical behavior of normal myocardium;

(3) The stable conductive myocardial patch with negative Poisson's ratio structure can be implanted into a human myocardial infarction site through thoracoscopic surgery. To a certain extent, it provides a way of thinking to avoid the complicated process of thoracotomy, postoperative complications, and long recovery time;

(4) The stable conductive myocardial patch with negative Poisson's ratio structure adopts textile molding and surface finishing technology. The preparation method is simple, cost-saving, and easy to realize industrialization.

BRIEF DESCRIPTION OF THE DRAWINGS

FIG. 1 shows a schematic diagram of negative Poisson's ratio structural model;

FIGS. 2A-2C show schematic diagrams of woven concave polygonal negative Poisson's ratio myocardial patch, wherein FIG. 2A shows a concave quadrilateral patch, FIG. 2B shows a symmetrical concave quadrilateral patch, and FIG. 2C shows a concave hexagon patch, 1 indicates weave 1 in FIG. 3, 2 indicates weave 2 in FIG. 3, and 3 indicates weave 3 in FIG. 3;

FIGS. 3A-3C show fabric weave charts, in which FIG. 3A shows a fabric weave chart of plain weave, FIG. 3B shows a fabric weave chart of twill weave, and FIG. 3C shows a fabric weave chart of satin weave;

DETAILED DESCRIPTION OF THE EMBODIMENTS

Figure 3A:
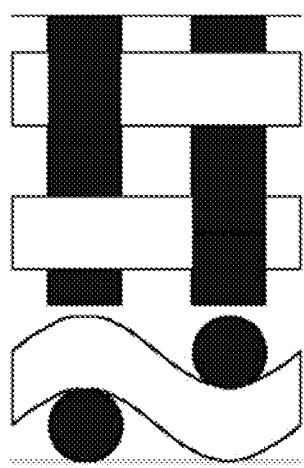
Figure 3B:
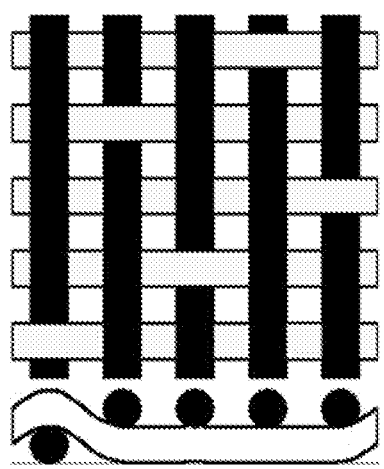
Figure 3C:
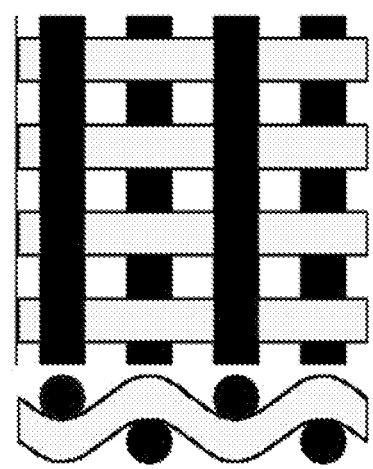

This invention is further explained below in conjunction with specific embodiments. It should be understood that these embodiments are only used to illustrate the present invention and not to limit the scope of the present invention. In addition, it should be understood that after reading the teachings of the present invention, those skilled in the art can make various changes or modifications to the present invention, and these equivalent forms also fall within the scope defined by the appended claims of the present application.

A stable conductive myocardial patch with a negative Poisson's ratio structure is a knitted fabric or woven fabric with a concave polygon as a structural unit; the knitted fabric or woven fabric is composed of yarns with conductive coatings on its surface.

The initial conductivity of the myocardial patch is 1-10 S/m, and the relative resistance change is less than 5% at 50% tensile strain. When the strain of the structural units is within 50%, the minimum Poisson's ratio of the knitted fabric is −0.5, and the minimum Poisson's ratio of the woven fabric is −0.1; and it expands in the perpendicular direction of the tensile load. The anisotropy ratio of Young's modulus of the myocardial patch is 1.99-5.71.

The structural unit is composed of yarns with different elasticities, and the weaves formed by the elastic yarns pull the surrounding weaves to shrink and fold.

The concave polygonal structural units in the woven fabric are composed of weaves 1, 2, and 3 of yarns with different contractility; among them, weaves 1, 2, and 3 have sequentially decreasing fabric densities; the structural units in the knitted fabric are half loops and half floats in the course where the elastic yarns are located.

Weave 1 is a plain weave, weave 2 is a twill weave or a satin weave, and weave 3 is a weave in which the warp yarns alternately float on the weft yarns.

The warp yarns of the woven fabric are composed of elastic yarns and inelastic yarns with a number ratio of 1:1, and the weft yarns are composed of elastic yarns or are composed of elastic yarns and inelastic yarns with a number ratio of 1:1; the yarns in the knitted fabric are composed of inelastic yarns and elastic yarns with a number ratio of 2:1.

The chemical composition of the elastic yarn is polycaprolactone or polyurethane, and the non-elastic yarn is polylactic acid.

The concave polygon is a concave quadrilateral, a symmetrical concave quadrilateral, or a concave hexagon.

The conductive coating is mainly made by the polymerization reaction of conductive polymer monomers, dopants, and oxidants.

When the conductive material monomer is pyrrole, the dopant is sodium dodecylbenzene sulfonate or cetyltrimethylammonium bromide, and the oxidant is ammonium persulfate or ferric chloride;

or, when the conductive material monomer is aniline, the dopant is hydrochloric acid, sulfuric acid, nitric acid, camphorsulfonic acid or sodium dodecylbenzene sulfonate, and the oxidant is ammonium persulfate, potassium dichromate, ferric chloride, or potassium iodate;

or, when the conductive material monomer is thiophene, the dopant is sodium dodecylbenzene sulfonate or cetyltrimethylammonium bromide, and the oxidant is iron trichloride, copper perchlorate, aluminum trichloride, or ammonium sulfate.

The method for preparing a stable conductive myocardial patch with a negative Poisson's ratio structure characterized in that: the myocardial patch substrate with concave polygonal structural units is manufactured by weaving or knitting, and then a conductive coating is coated on the surface of the substrate by coating and in-situ polymerization to obtain a conductive and stable myocardial patch with a negative Poisson's ratio structure;

or, the yarns can be processed into conductive yarns first by coating and in-situ polymerization, and then the conductive yarns are used as the raw material to weave or knit a stable conductive myocardial patch with a negative Poisson's ratio structure.

The process of processing the conductive polymer onto the myocardial patch substrate by the in-situ polymerization method is:

(1) The oxidant and dopant are added to the 10-40 wt % polyurethane solution and stirred evenly;

(2) The surface of the myocardial patch substrate is coated with polyurethane solution 1-10 times;

(3) The coated substrate is fumigated with conductive material monomer at 0-60° C. for 1-24 h.

The process of fabricating the conductive polymer onto the yarns by the in-situ polymerization method is:

(1) The conductive polymer monomer and dopant are added to the 10-40 wt % polyurethane solution and stirred evenly;

(2) The yarns are immersed in the mixed solution for 1-30 min;

(3) The coated yarns are immersed in or coated with the oxidant solution at 0-60° C. for 1-24 h.

(4) After washing with deionized water 1 to 5 times, the conductive yarns are obtained after being dried;

The process of surface coating is:

(1) The conductive polymer monomer and dopant are added to the oxidant solution and stirred, and then allowed to polymerize for 3-6 h;

(2) After polymerization, the conductive polymer powder is obtained by filtration and drying;

(3) A certain mass of conductive polymer powder is added to the 10-40 wt % polyurethane solution and stirred evenly;

(4) The surface of the myocardial patch substrates or yarns are coated with the solution 1 to 10 times, and a stable conductive myocardial patch or conductive yarns with a negative Poisson's ratio structure are prepared after being dried.

The method for preparing a stable conductive myocardial patch with a negative Poisson's ratio structure characterized in that when weaving technology is used, the specific steps are as follows:

(1) The yarns or conductive yarns are woven on a loom to obtain a fabric;

(2) The fabric is soaked in deionized water at a temperature of 50-70° C. for 20-60 min, and dried in a drum at 60-100° C. for 30-60 min;

(3) The fabric is relaxed for 12-24 h to obtain a woven fabric.

When using knitting technology, the specific steps are as follow:

(1) The yarns or conductive yarns is fed in and knitted on the computerized flat knitting machine to obtain the fabric;

(2) The fabric is soaked in deionized water at a temperature of 50-70° C. for 20-60 min, and drum-dried at 60-100° C. for 30-60 min;

(3) The fabric is relaxed for 12-24 h to obtain a knitted fabric.

FIG. 1 shows a schematic diagram of the negative Poisson's ratio structure model. It can be seen from the figure that when a negative Poisson material with a concave polygonal structure is stretched, it will expand in the perpendicular direction of the stretching load.

EXAMPLE 1

The method for preparing a stable conductive myocardial patch with a negative Poisson's ratio structure, including the following steps:

(1) The pyrrole monomer is added to the $FeCl_3$ solution and stirred for 4 h; after polymerization, the polypyrrole powder is obtained by filtration and drying (The molar ratio of $FeCl_3$ to pyrrole monomer is 2.3:1);

(2) The polypyrrole powder is added to the 30 wt % polyurethane solution and stirred to obtain a homogenous 30 wt % polypyrrole suspension;

(3) Polyurethane yarns and polylactic acid yarns are immersed in the above suspension for 5 minutes.

Figure 4:
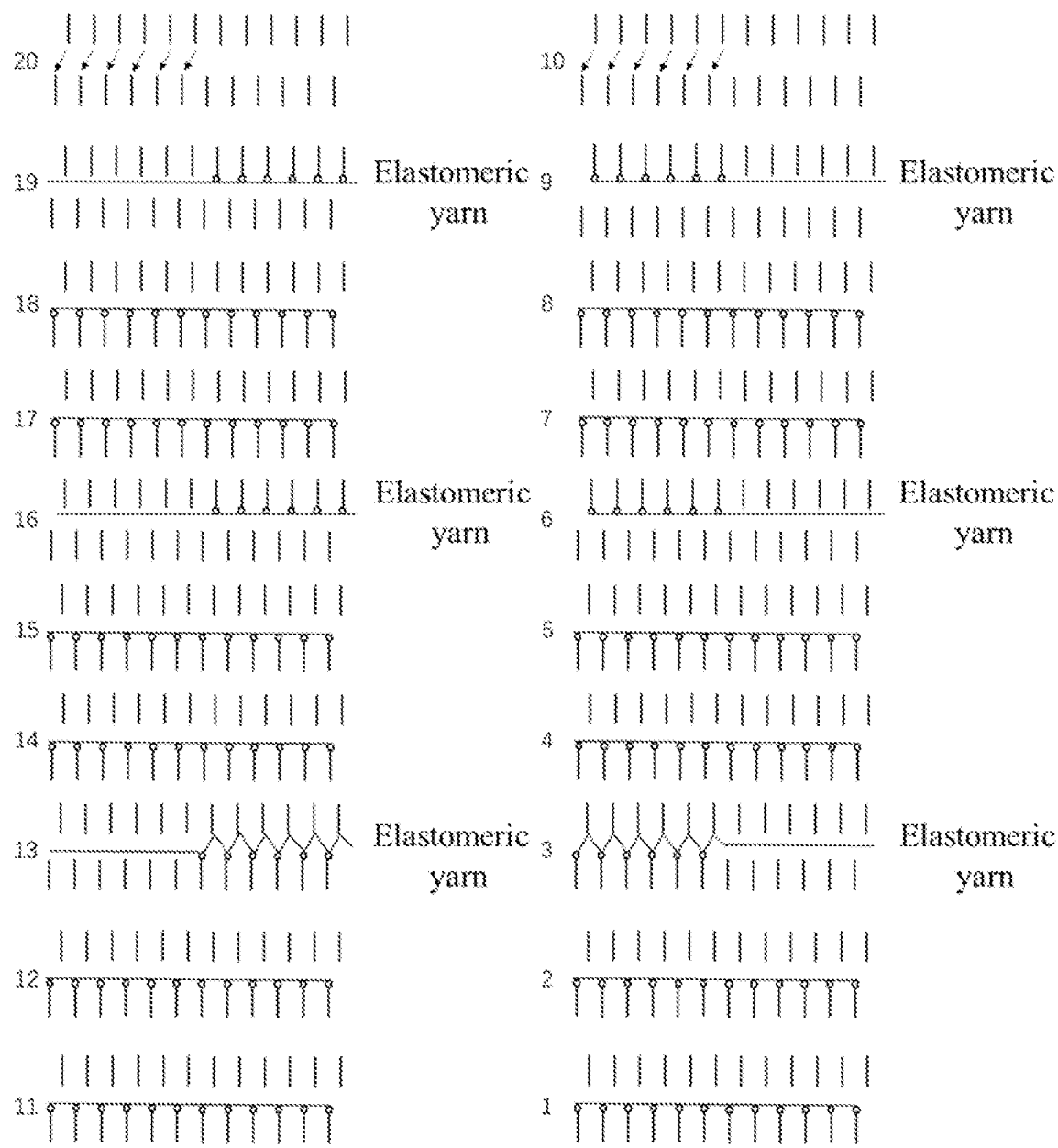
FIG. 4 shows a knitting diagram of the myocardial patch with a concave hexagonal negative Poisson's ratio structure.

(4) The polypyrrole-coated polyurethane yarns and the polypyrrole-coated polylactic acid yarns are prepared after washing and drying;

(5) The conductive yarns are fed in and knitted on the computerized flat knitting machine according to the knitting diagram shown in FIG. 4 to obtain the fabric (the polypyrrole-coated polylactic acid yarns and polypyrrole-coated polyurethane yarns are arranged alternately in number ratio of 2:1);

(6) After being relaxed from the machine, the fabric naturally shrinks and folds to form a stable conductive myocardial patch with a negative Poisson's ratio structure;

The initial conductivity of the myocardial patch is 3 S/m, and the relative resistance change is less than 5% at 50% tensile strain. When the strain of the structural units is within 50%, the minimum Poisson's ratio of the fabric is −0.5 and it expands in the perpendicular direction of the tensile load. The anisotropy ratio of Young's modulus of the myocardial patch is 3.8.

EXAMPLE 2

The method for preparing a stable conductive myocardial patch with a negative Poisson's ratio structure, including the following steps:

(1) The polycaprolactone yarns and polylactic acid yarns are fed in and knitted on the computerized flat knitting machine according to the knitting diagram shown in FIG. 4 to obtain the fabric (the polypyrrole-coated polylactic acid yarns and polypyrrole-coated polyurethane yarns are arranged alternately in number ratio of 2:1);

(2) Before being relaxed from the machine, the fabric is coated by the polyurethane solution (10% w/v) containing sodium dodecylbenzene sulfonate (1% w/v) and ammonium persulfate (3% w/v) three times;

(3) The coated fabric is fumigated with pyrrole monomer at 4° C. for 12 h;

(4) After being relaxed from the machine, the fabric is soaked in deionized water at 60° C. for 40 min, and dried in a drum at 70° C. for 60 min;

(5) The fabric is relaxed for 24 h to obtain a knitted fabric.

The initial conductivity of the myocardial patch is 5 S/m, and the relative resistance change is less than 3% at 50% tensile strain. When the strain of the structural units is within 50%, the minimum Poisson's ratio of the fabric is −0.5 and it expands in the perpendicular direction of the tensile load. The anisotropy ratio of Young's modulus of the myocardial patch is 2.78.

EXAMPLE 3

The method for preparing a stable conductive myocardial patch with a negative Poisson's ratio structure, including the following steps:

(1) Polycaprolactone yarn is used as elastic yarn raw material, and polylactic acid yarn is used as inelastic yarn, and a rapier loom with two kinds of weft yarn supplies and dobby shedding mechanism is used;

(2) The warp yarns (polycaprolactone yarns and polylactic acid yarns arranged alternatively at a number ratio of 1:1) are used for winding, warping, sizing, and drawing-in, and polycaprolactone yarn is selected as the weft yarn. The myocardial patch substrate is prepared according to FIG. 2A and FIGS. 3A-3C.

(3) Before being relaxed from the machine, the fabric is coated by the polyurethane solution (10% w/v) containing sodium dodecylbenzene sulfonate (1% w/v) and ammonium persulfate (3% w/v) three times;

(4) The coated fabric is fumigated with pyrrole monomer at 4° C. for 12 h;

(5) After being relaxed from the machine, the fabric is soaked in deionized water at 60° C. for 40 min, and dried in a drum at 70° C. for 60 min;

(6) The fabric is relaxed for 24 h to obtain a woven fabric.

The initial conductivity of the myocardial patch is 8 S/m, and the relative resistance change is less than 3% at 50% tensile strain. When the strain of the structural units is within 50%, the minimum Poisson's ratio of the fabric is −0.08 and it expands in the perpendicular direction of the tensile load. The anisotropy ratio of Young's modulus of the myocardial patch is 1.99.

EXAMPLE 4

The method for preparing a stable conductive myocardial patch with a negative Poisson's ratio structure, including the following steps:

(1) Polycaprolactone yarn is used as elastic yarn raw material, and polylactic acid yarn is used as inelastic yarn, and a rapier loom with two kinds of weft yarn supplies and dobby shedding mechanism is used;

(2) The warp yarns (polycaprolactone yarns and polylactic acid yarns arranged alternatively at a number ratio of 1:1) are used for winding, warping, sizing, and drawing-in, and polycaprolactone yarn is selected as the weft yarn. The myocardial patch substrate is prepared according to FIG. 2B and FIGS. 3A-3C.

(3) Before being relaxed from the machine, the fabric is coated by the polyurethane solution (10% w/v) containing sodium dodecylbenzene sulfonate (1% w/v) and ammonium persulfate (3% w/v) three times;

(4) The coated fabric is fumigated with pyrrole monomer at 4° C. for 12 h;

(5) After being relaxed from the machine, the fabric is soaked in deionized water at 60° C. for 40 min, and dried in a drum at 70° C. for 60 min;

(6) The fabric is relaxed for 24 h to obtain a woven fabric.

The initial conductivity of the myocardial patch is 8 S/m, and the relative resistance change is less than 5% at 50% tensile strain. When the strain of the structural units is within 50%, the minimum Poisson's ratio of the fabric is −0.1 and it expands in the perpendicular direction of the tensile load. The anisotropy ratio of Young's modulus of the myocardial patch is 2.35.

EXAMPLE 5

The method for preparing a stable conductive myocardial patch with a negative Poisson's ratio structure, including the following steps:

(1) Polycaprolactone yarn is used as elastic yarn raw material, and polylactic acid yarn is used as inelastic yarn, and a rapier loom with two kinds of weft yarn supplies and dobby shedding mechanism is used;

(2) The warp yarns (polycaprolactone yarns and polylactic acid yarns arranged alternatively at a number ratio of 1:1) are used for winding, warping, sizing, and drawing-in, and polycaprolactone yarn is selected as the weft yarn. The myocardial patch substrate is prepared according to FIG. 2C and FIGS. 3A-3C.

(3) Before being relaxed from the machine, the fabric is coated by the polyurethane solution (10% w/v) containing sodium dodecylbenzene sulfonate (1% w/v) and ammonium persulfate (3% w/v) three times;

(4) The coated fabric is fumigated with pyrrole monomer at 4° C. for 12 h;

(5) After being relaxed from the machine, the fabric is soaked in deionized water at 60° C. for 40 min, and dried in a drum at 70° C. for 60 min;

(6) The fabric is relaxed for 24 h to obtain a woven fabric.

The initial conductivity of the myocardial patch is 8 S/m, and the relative resistance change is less than 5% at 50% tensile strain. When the strain of the structural units is within 50%, the minimum Poisson's ratio of the fabric is −0.08 and it expands in the perpendicular direction of the tensile load. The anisotropy ratio of Young's modulus of the myocardial patch is 2.41.

EXAMPLE 6

The method for preparing a stable conductive myocardial patch with a negative Poisson's ratio structure is the same as in Example 5. The difference lies in the methods for conductive coating on the fabric in steps (3) to (6), specifically as follows:

(3) The pyrrole monomer and sodium dodecylbenzene sulfonate are added to the ammonium persulfate solution and stirred for 5 h; after polymerization, the polypyrrole powder is obtained by filtration and drying (The molar ratio of pyrrole monomer, sodium dodecylbenzene sulfonate, and ammonium persulfate is 1:0.8:1);

(4) The polypyrrole powder is added to the 30 wt % polyurethane solution and stirred to obtain a homogenous 30 wt % polypyrrole suspension;

(5) The surface of the substrate is coated with the solution 3 times. And after air drying, a conductive and stable myocardial patch with a negative Poisson's ratio structure is prepared;

The initial conductivity of the myocardial patch is 8 S/m, and the relative resistance change is less than 5% at 50% tensile strain. When the strain of the structural units is within 50%, the minimum Poisson's ratio of the fabric is −0.08 and it expands in the perpendicular direction of the tensile load. The anisotropy ratio of Young's modulus of the myocardial patch is 2.41.

EXAMPLE 7

To explore the effect of a myocardial patch matching the electrical and mechanical behavior of normal myocardium on myocardial repair in Examples 1 to 6, the steps are as follows:

(1) Sprague-Dawley rats are anesthetized with moderate ether, followed by left thoracic incisions to expose the heart, and then the left coronary arteries are ligated with 8-0 #sutures 2 mm below the left atrial appendage to establish rat myocardial infarction models;

(2) Myocardial infarcted Sprague-Dawley rats are divided into two groups: the sham group and the experimental group in which each rat is transplanted with a conductive myocardial patch with a negative Poisson's ratio structure;

(3) After 2 weeks, the heart function of the rats is observed using echocardiography. The rats are euthanized and their heart tissues are collected and fixed in 4% paraformaldehyde at 4° C. and dehydrated in ethanol. Masson's trichrome staining is performed on the frozen sections to observe the changes in fibrotic tissue, infarct area, and left ventricular wall thickness.

Experimental results showed that implanting a conductive fabric with a negative Poisson's ratio structure into the heart of rats with myocardial infarction can significantly increase the cardiac ejection fraction and the shortening fraction of the left ventricular axis, and significantly reduce the size of the left ventricle during systole as well as the size of the fibrotic tissue and infarct area.

EXAMPLE 8

To explore the effect of a myocardial patch matching the electrical and mechanical behavior of normal myocardium on myocardial repair in Examples 1 to 6, the steps are as follows:

(1) Neonatal rat cardiomyocytes are seeded on a conductive myocardial patch with a negative Poisson's ratio structure at a density of $5 \times 10^6$ cells/cm$^2$. Cardiomyocytes are cultured in high-glucose Dulbecco's modified Eagle medium supplemented with 15% fetal bovine serum, 100 U/ml penicillin, and 100 ug/ml streptomycin. Cells are incubated at 37° C. under 5% $CO_2$, and the medium is changed every two days.

(2) After the cardiomyocytes are cultured for 7 days, the viability of the cardiomyocytes on the myocardial patch is measured by live/dead cell staining.

(3) Sprague-Dawley rats are anesthetized with moderate ether, followed by left thoracic incisions to expose the heart, and then the left coronary arteries are ligated with 8-0 #sutures 2 mm below the left atrial appendage to establish rat myocardial infarction models. Myocardial infarcted Sprague-Dawley rats are divided into two groups: the sham group and the experimental group in which each rat is transplanted with a cardiomyocytes-loaded conductive myocardial patch with a negative Poisson's ratio structure;

(4) The echocardiography system is used to evaluate the left ventricular function of rats at 3, 7, 14, and 28 days after surgery.

(5) After 4 weeks, the heart function of the rats is observed using echocardiography. The rats are euthanized, and their heart tissues are collected and fixed in 4% paraformaldehyde at 4° C. and dehydrated in ethanol. Masson's trichrome staining is performed on the frozen sections to observe the changes in fibrotic tissue, infarct area, and left ventricular wall thickness.

The experimental results showed that the viability of cardiomyocytes cultured on the myocardial patch was not significantly different from that cultured on the petri dish, and the myocardial patch had good biocompatibility. After the patch was implanted into the myocardial infarcted rats, the cardiac ejection fraction and the shortening fraction of the left ventricular short-axis were significantly increased. The internal size of the left ventricle decreased significantly during systole, and the size of fibrotic tissue and infarct area were also reduced.

What is claimed is:

1. A conductive myocardial patch with stable conductive performance and a negative Poisson's ratio structure, comprising a woven fabric with a concave polygon as a structural unit, wherein the woven fabric is composed of yarns with a conductive coating on a surface of the yarns,
    wherein the conductive coating is synthesized by a polymerization reaction of a conductive polymer monomer, a dopant, and an oxidant,
    wherein an initial conductivity prior to stretching of the conductive myocardial patch is 1-10 S/m, and
    when the conductive myocardial patch is stretched: a relative resistance change is less than 5% at 50% tensile strain;
    when a strain of the structural unit is within 50%, a minimum Poisson's ratio of the woven fabric is −0.1; and
    the conductive myocardial patch expands in a perpendicular direction of a tensile load, and an anisotropy ratio of Young's modulus of the conductive myocardial patch is 1.99-5.71;
    wherein
    the yarns are yarns with different elasticities, and the yarns with different elasticities comprise elastic yarns and inelastic yarns, and
    the structural unit in the woven fabric is composed of a first weave, a second weave, and a third weave interwoven by the yarns with different elasticities, wherein the first weave, the second weave and the third weave have sequentially decreasing fabric densities, and
    wherein the first weave is a plain weave, the second weave is a twill weave or a satin weave, and the third weave is a weave having warp yarns alternately floating on weft yarns, and
    wherein the densities of the warp yarns and the weft yarns are 30 yarns/cm and 25 yarns/cm, respectively.

2. The conductive myocardial patch according to claim 1, wherein the structural unit formed by the elastic yarns pulls surrounding units to shrink and fold.

3. The conductive myocardial patch according to claim 1, wherein
    warp yarns of the woven fabric are composed of the elastic yarns and the inelastic yarns with a number ratio of 1:1, and the weft yarns are composed of the elastic yarns separately or are composed of the elastic yarns and the inelastic yarns with a number ratio of 1:1.

4. The conductive myocardial patch according to claim 3, wherein a chemical composition of the elastic yarns is polycaprolactone or polyurethane, and a chemical composition of the inelastic yarns is polylactic acid.

5. The conductive myocardial patch according to claim 1, wherein the concave polygon is a concave quadrilateral, a symmetrical concave quadrilateral, or a concave hexagon.

6. The conductive myocardial patch according to claim 1, wherein
when the conductive polymer monomer is pyrrole, the dopant is sodium dodecylbenzene sulfonate or cetyltrimethylammonium bromide, and the oxidant is ammonium persulfate or ferric chloride;
or, when the conductive polymer monomer is aniline, the dopant is hydrochloric acid, sulfuric acid, nitric acid, camphorsulfonic acid or sodium dodecylbenzene sulfonate, and the oxidant is ammonium persulfate, potassium dichromate, ferric chloride, or potassium iodate;
or, when the conductive polymer monomer is thiophene, the dopant is sodium dodecylbenzene sulfonate or cetyltrimethylammonium bromide, and the oxidant is iron trichloride, copper perchlorate, aluminum trichloride, or ammonium sulfate.

7. A method for preparing the conductive myocardial patch according to claim 1, comprising
manufacturing a myocardial patch substrate with concave polygonal structural units by weaving, and then applying the conductive coating on a surface of the myocardial patch substrate by coating and in-situ polymerization to obtain the conductive myocardial patch with the negative Poisson's ratio structure;
or, applying the conductive coating on the yarns first by coating and the in-situ polymerization to obtain conductive coated yarns, and then using the conductive coated yarns as a raw material to weave the conductive myocardial patch with the negative Poisson's ratio structure.

8. The method according to claim 7, wherein the step of fabricating the conductive coating of the myocardial patch substrate by the in-situ polymerization comprises:
1) adding the oxidant and the dopant to a 10-40 wt % polyurethane solution and stirring evenly;
2) coating the surface of the myocardial patch substrate with the 10-40 wt % polyurethane solution 1-10 times to obtain a coated substrate; and
3) fumigating the coated substrate with a conductive material monomer at 0-60° C. for 1-24 h;
a process of fabricating a conductive polymer coating of the yarns by the in-situ polymerization method comprises:
1) adding the conductive polymer monomer and the dopant to the 10-40 wt % polyurethane solution and stirring evenly to obtain a mixed solution;
2) immersing the yarns with the mixed solution for 1-30 min to obtain coated yarns;
3) immersing or coating the coated yarns in a solution of the oxidant at 0-60° C. for 1-24 h to obtain the conductive coated yarns; and
4) after washing the conductive coated yarns with deionized water 1 to 5 times, then drying and collecting the conductive coated yarns; and
a process of surface coating comprises:
1) adding the conductive polymer monomer and the dopant to the solution of the oxidant and stirring, and then performing a polymerization for 3-6 h;
2) after the polymerization, obtaining a conductive polymer powder by filtration and drying;
3) adding a certain mass of the conductive polymer powder to the 10-40 wt % polyurethane solution and stirring evenly to obtain a homogenous suspension;
4) coating the surface of the myocardial patch substrate or the yarns with the homogenous suspension 1 to 10 times, and drying to prepare the conductive myocardial patch or the conductive coated yarns with the negative Poisson's ratio structure.

9. The method according to claim 7, wherein
the weaving comprises the following steps:
1) weaving the yarns or the conductive coated yarns on a loom to obtain a preliminary woven fabric;
2) soaking the preliminary woven fabric in deionized water at a temperature of 50-70° C. for 20-60 min, and drying in a drum at 60-100° C. for 30-60 min to obtain a treated woven fabric; and
3) relaxing the treated woven fabric for 12-24 h to obtain the woven fabric.

10. The method according to claim 7, wherein the structural unit formed by the elastic yarns pull surrounding units to shrink and fold.

11. The method according to claim 7, wherein
warp yarns of the woven fabric are composed of the elastic yarns and the inelastic yarns with a number ratio of 1:1, and the weft yarns are composed of the elastic yarns separately or are composed of the elastic yarns and the inelastic yarns with a number ratio of 1:1.

12. The method according to claim 11, wherein a chemical composition of the elastic yarns is polycaprolactone or polyurethane, and a chemical composition of the inelastic yarns is polylactic acid.

13. The method according to claim 7, wherein the concave polygon is a concave quadrilateral, a symmetrical concave quadrilateral, or a concave hexagon.

14. The method according to claim 7, wherein
when the conductive polymer monomer is pyrrole, the dopant is sodium dodecylbenzene sulfonate or cetyltrimethylammonium bromide, and the oxidant is ammonium persulfate or ferric chloride;
or, when the conductive polymer monomer is aniline, the dopant is hydrochloric acid, sulfuric acid, nitric acid, camphorsulfonic acid or sodium dodecylbenzene sulfonate, and the oxidant is ammonium persulfate, potassium dichromate, ferric chloride, or potassium iodate;
or, when the conductive polymer monomer is thiophene, the dopant is sodium dodecylbenzene sulfonate or cetyltrimethylammonium bromide, and the oxidant is iron trichloride, copper perchlorate, aluminum trichloride, or ammonium sulfate.

* * * * *